United States Patent
Lentini

(10) Patent No.: US 8,689,005 B2
(45) Date of Patent: Apr. 1, 2014

(54) METHOD FOR MANAGING AND CONTROLLING ACCESS TO CONFIDENTIAL INFORMATION CONTAINED IN PORTABLE ELECTRONIC MEDIA

(76) Inventor: Carlo Lentini, Grottaferrata (IT)

( * ) Notice: Subject to any disclaimer, the term of this patent is extended or adjusted under 35 U.S.C. 154(b) by 0 days.

(21) Appl. No.: 13/322,036

(22) PCT Filed: Feb. 10, 2010

(86) PCT No.: PCT/IT2010/000044
§ 371 (c)(1),
(2), (4) Date: Nov. 22, 2011

(87) PCT Pub. No.: WO2010/137047
PCT Pub. Date: Dec. 2, 2010

(65) Prior Publication Data
US 2012/0066508 A1 Mar. 15, 2012

(30) Foreign Application Priority Data
May 26, 2009 (IT) .............................. RM2009A0267

(51) Int. Cl.
*G06F 21/00* (2013.01)
(52) U.S. Cl.
USPC ............. 713/186; 713/193; 713/176; 726/28; 705/2; 705/3; 705/51
(58) Field of Classification Search
USPC ........................................................ 713/186
See application file for complete search history.

(56) References Cited

U.S. PATENT DOCUMENTS

| | | | |
|---|---|---|---|
| 6,775,774 | B1 | 8/2004 | Harper |
| 7,661,146 | B2* | 2/2010 | Karimzadeh et al. ........... 726/27 |
| 2004/0128502 | A1* | 7/2004 | Royer ............................ 713/156 |
| 2005/0197859 | A1* | 9/2005 | Wilson et al. ...................... 705/2 |
| 2007/0006322 | A1* | 1/2007 | Karimzadeh et al. ........... 726/27 |
| 2007/0016452 | A1* | 1/2007 | Wilson, III ........................ 705/3 |
| 2009/0076849 | A1 | 3/2009 | Diller |
| 2009/0182911 | A1* | 7/2009 | Krasner et al. .................. 710/63 |
| 2010/0179819 | A1* | 7/2010 | Herbst et al. ...................... 705/2 |
| 2012/0066508 | A1* | 3/2012 | Lentini ........................ 713/186 |

OTHER PUBLICATIONS

International Search Report, dated Apr. 27, 2010, from corresponding PCT application.

* cited by examiner

*Primary Examiner* — Michael R Vaughan
(74) *Attorney, Agent, or Firm* — Young & Thompson

(57) ABSTRACT

A method of the management for confidential information contained in portable memory media provides recognition by a biometric identification element of the individual who is the proprietor of the information in the proprietor medium; recognition by a biometric identification element of an interlocutor individual, set for inserting and managing the confidential information, who in turn possesses an interlocutor memory medium with identification functions; automatic interfacing and matching between the proprietor medium and the interlocutor medium in terms of user identifications in order to authenticate the access to the stored information on the basis of the preconfigured access permissions; and attachment of a digital signature based on an asymmetric key for the updated/modified information stored on the proprietor medium and on the interlocutor medium.

15 Claims, 2 Drawing Sheets

METHOD FOR MANAGING AND CONTROLLING ACCESS TO CONFIDENTIAL INFORMATION CONTAINED IN PORTABLE ELECTRONIC MEDIA

FIELD OF THE INVENTION

The present invention generally refers to the problem of data privacy and security in accessing confidential data; more particularly it deals with a system and related method for controlling the management and the controlled diffusion of confidential digital information contained in portable electronic media, with particular regard to the information of interest for the users of the system itself.

BACKGROUND OF THE INVENTION

Archives are a precious resource for any company, and they can usually be used by several applications and handled by a number of people. The security problems connected with the archives mainly regard the aspects of data loss and non-authorized access to information. This second point related to data privacy and information security is of specific interest in the present document. Normally it is based on a centralized security capable of distributing the authorizations and the access modes. Generally, a profile is associated with every user whose access is controlled via password. However, it is known how the protection mechanism via ID and password has for some time been outmoded due to the dangers of intrusion that it presents. Among the most serious and dangerous access techniques, one need only mention sniffing as an example—this provides for the interception of the packet moving on the network in order to obtain its access and validation information, such as the key words, enabling codes or credit card numbers etc.

Another important aspect of the problem is the possibility to access the data through the Internet, e.g. by means of HTTP navigation services or FTP data download services. Since reference will be made below to applications of the finding in the medical/hospital sector, it is relevant to evaluate the inadequacy of some measures taken, starting from the most striking cases of this field.

A recent report by Cisco Systems indicated that one out of four administrators admitted having a security system "hole" in the last 12 months.

The theme of privacy has for some time been confronted by mammoths like Google and Microsoft. According to a recent estimate made by the same, since 60% of Internet navigators query the search engine to receive health-related information, a database so vast that collects the health information of millions of people would be incredibly valuable for Big Pharma marketing and would constitute an unacceptable monopoly of health information not bound by any law. Thus, both Google and Microsoft have produced services that allow managing the personal clinical file; however, from a study published in the British Medical Journal in the spring, which evaluated an experience similar to that proposed by Google and Microsoft that was activated by the British Health minister, it emerged that British citizens do not use on-line clinical health files since they fear that their data is not safe.

The scenario is therefore complex, and the Internet-based model is not appreciated for the above-described reasons. In addition, just the digitalization operation of all the image diagnostics, from the plates to the CAT scans, requires a significant expense, even if there will be a savings equal to half the sustained investment essentially due to the fact that the liquids required for film development will no longer have to be purchased. However, these costs are found on the balance sheet in another entry: data communication network. Transmitting a radiographic image involves long wait times and technology management costs.

It is therefore of fundamental importance to devise a solution that:

a—is not bound by the technical bias which states that the data archive must be localized and accessed via the Internet, and b—restores, to the single user, the "physical" properties of the confidential information belonging thereto.

More generally, it should be noted that in the present context with the writing "auxiliary memory device", reference is generally made to removable memory media capable of being preserved in environments protected from unauthorized intrusions and from possible damage to the same or to the equipment containing them. They can be inserted in a personal computer; they can be inserted in a Server machine; they can also be inserted in mobile devices (such as cell phones, disks, DVD/CD players, pen drives, removable hard disks, SD cards, PCMCIA cards, etc.) in order to allow their diffusion and management.

It is known that the information of confidential character stored on a portable electronic device has the problem that it can be viewed by anyone; even if security systems are used, these might well be eluded. In addition, the information displayed on a computer system can be easily duplicated and transmitted from one computer to another.

The object of the present invention is a system and related method for the controlled management and controlled diffusion of confidential digital information which ensures that the two subjects, each time they are interested in sharing information, are recognized by the system in an automatic and secure manner; in addition, the identify of both subjects is ascertained in an unequivocal manner, with no possibility of intrusion of third party subjects during the entire confidential information management step. It is required that each of the subjects simultaneously use their own electronic medium in order to be able to share the management and controlled diffusion of confidential digital information contained in the portable electronic medium.

BRIEF SUMMARY OF THE INVENTION

The object of the present invention is that of providing a control technique for the controlled management of the information contained in removable electronic media which is characterized by a distributed and non-centralized architecture, (precisely to the contrary of the widespread techniques mentioned above, which provide for a centralized responsibility) and hence in which the two-person relationship between the single data proprietor and the relative interlocutor is favored. The peer-to-peer diction is not used here in the original meaning, i.e. telecommunications network configuration in which two PCs mutually exchange the roles of client and server. Here, instead, the characterizing principle is taken which provides for the sharing of several files on the basis of preconfigured access rights for the two users, and since each user takes the decisions locally the network does not have a central control point or a centralized administration (however one wishes to call it).

The object of the present invention is also that in the specific application context of a health system, the relations between the patient and the public body and/or private supplier of the service are facilitated, and the duplication of the biochemical, semiotic instruments is avoided, reducing the costs. Above all, it allows the diffusion of one's health data to all visited structures, so that no one has an exclusive access to the data, allowing the patient the possibility to access his data from a simple computer without there being a request to install programs or particular electronic systems, which is however required when one uses the national health card.

The final object of the present invention is that of providing a control technique for the management and controlled diffusion of confidential data contained in portable electronic media which employs the most common operating systems and communication access protocols, those recognized as standards in the context of data security control, for the purpose of making the obtainment of the finding prompt, reliable and easy to manage and maintain.

These and other objects which will be clear during the description are obtained with a control technique for the management and controlled diffusion of confidential digital data contained in portable electronic media, whose fundamental principles are explained in the enclosed claims.

BRIEF DESCRIPTION OF THE DRAWINGS

For the sole purpose of better clarifying the invention, without wishing to limit its scope and the fields in which it can be applied, several particular embodiments will be described below with reference to the enclosed Figures. Such embodiments will be merely provided as examples with reference to the drawings in which.

DETAILED DESCRIPTION OF THE INVENTION

Figure 1:
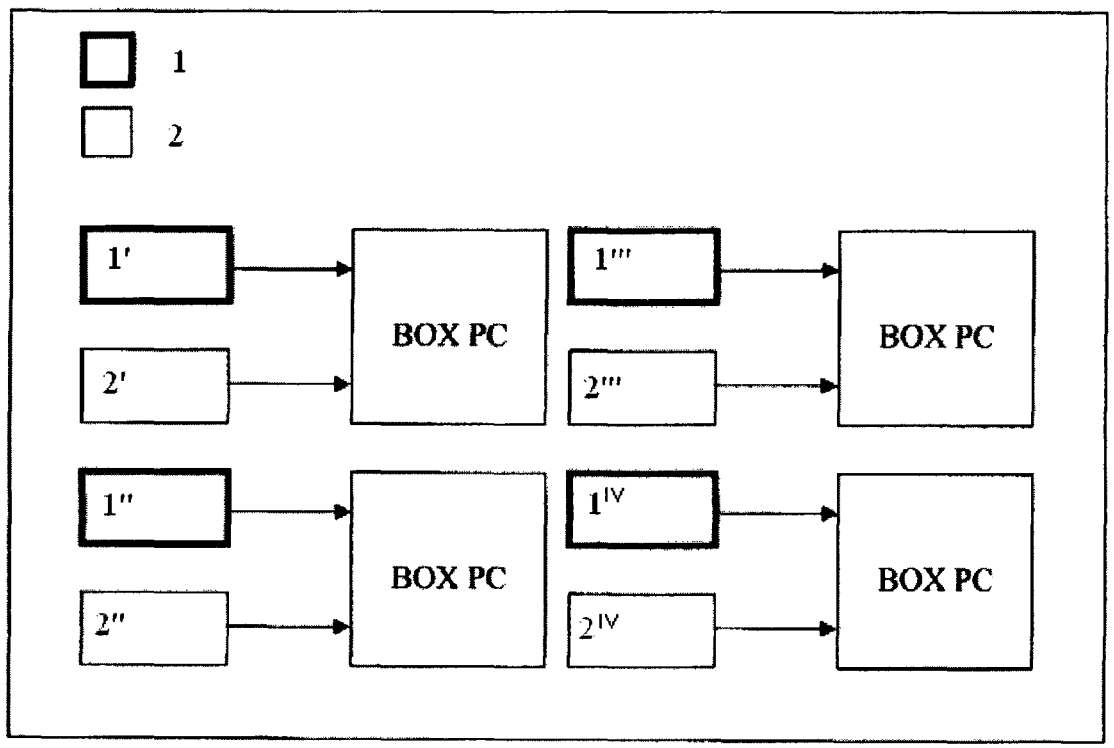
FIG. 1 is an approximate block diagram.

The fundamental principle for the present invention is that the stored confidential information is and must remain the property of the citizen/individual and only this person can give the authorization to others for their modification and/or extrapolation. The proprietor is provided with a "memory medium", which consists of a pen drive or a SD card of removable type, used for storing the digital data (media which have substituted traditional floppy disks, for some time now). Such memory medium is provided with a biometric recognizer (for example a digital fingerprint recognizer) and thus allows the person possessing this to be able to "authorize" the access to the digital data stored therein, only after the recognition of the biometric identification has occurred. In this manner, the information will only be visible to the proprietor and possibly to whomever the proprietor wishes. At the same time, each proprietor subject will be assigned his own interlocutor subject—he too supplied with one access key with biometric identification—with which he interworks when an update of the information on the memory medium is requested.

Even if, as stated, the finding has a general value, in its specific application in the health sector the proprietor—i.e. the patient—will only be able to view the health data stored on his own biometric memory device; he cannot modify it or add other data since the only one authorized to do so is the doctor who had another biometric memory device capable of enabling all the biometric memory devices of the people who come to him for health services.

The doctor also each time carries out the recognition of his own biometric identification on his own medium in order to be able to make these modifications, in a manner such that his identity is ensured. In addition, the method according to the present invention provides for a procedure of digital signature of the documents, since the digital certificate itself resides on the memory media of the doctor and patient.

As can be guessed, it is not necessary to be connected to the network, agreements between different producers are not necessary, and multiple pre-installed programs are not necessary because all that serves for the correct functioning is contained in the portable memory media. Above all it is not necessary to have a particular computer system, since a normal computer of any brand and type is sufficient in which the memory medium of the individual requesting the service is inserted at the same time as the memory medium of the interlocutor.

The enclosed drawing 1 indicates a distributed network architecture which shows a peer-to-peer work condition between single user/proprietor 1 and the related interlocutor 2.

DESCRIPTION OF A PREFERRED EMBODIMENT

In the present description, the following persons and instruments are identified and will be referred to; they operate by using the system and the related method for controlling the management and controlled diffusion of confidential digital information.

ADMINISTRATOR: is an organization which manages the service, packages the devices and assigns them to the authorized subjects, manages the delegates, retrieves and processes the information of statistical and economical type.

PROPRIETOR: is the individual 1, the proprietor of the confidential digital information stored on the portable electronic medium, who is identified with the term PROPRIETOR MEDIUM, assigned by the ADMINISTRATOR and thus owned by the same PROPRIETOR, who can disclose its own data, viewing it, but cannot modify it;

INTERLOCUTOR: is the individual 2 who is authorized by the SYSTEM to manage the confidential digital information of the proprietor contained in the PROPRIETOR MEDIUM. The management of the confidential digital information of the PROPRIETOR is carried out if and only if the recognition of the INTERLOCUTOR identity is made by means of comparing the information in a portable electronic medium owned by the interlocutor with the information detected from physical characteristics of the INTERLOCUTOR himself. The portable electronic medium, identified with the term "INTERLOCUTOR MEDIUM", is assigned by the administrator and thus is owned by the same interlocutor.

The proprietor subjects can delegate other subjects who can then be substituted for the delegator at any moment, even without his knowledge. The important thing is that the delegated subjects possess the digital medium containing the confidential digital information.

The operations of delegation, recognition of the delegator, recognition and storage of the information regarding the delegated party are prearranged before the operations of management and diffusion of the information. The delegation operations can be modified, and the modifications can be carried out by the service administrator.

In order to manage the security of the data stored on the removable memory medium, any one coding technique can be used. In other words, before being stored the data must undergo a coding that renders it illegible to everyone except the proprietor and the interlocutor authorized by the system for the management and controlled diffusion of the confidential information. The coding and decoding can be executed by one or more encryption algorithms. These algorithms implement the related mathematical functions and are used together with a key, usually a very large number.

Nevertheless, the possibility to violate the secrecy of the coded data is well known, by means of cryptanalysis techniques—above all if the coding occurs via symmetric key. According to the present invention, a particular use of the asymmetric keys (digital signature) is introduced for the protection of the data stored on the memory media.

It is well-known that the term "asymmetric key" refers to the fact that the system uses two keys (a public key for the coding, and a private key for the decoding or deciphering).

The two keys are mathematically correlated, so that the messages coded with the public key can only be decoded by the person who possesses the private key. The particular characteristic and the strength of this encryption system is that even if one knows the public key, it is not possible to uncover the corresponding private key.

The pair of keys is generated by a suitable software program. Each person who wishes to receive the coded messages must be supplied with a pair of keys: the private key is kept secret, while the public key is freely distributed to all the people with whom one wishes to communicate.

The sender of a message must know the public key of the receiver and subsequently he can code the message by using this key. The coded text can only be decoded by the person who possesses the private key correlated with the public key with which the message has been coded. The receiver, being in possession of this secret, private key, can read the message after having decoded it.

The advantage of the asymmetric key encryption system is that the sender and the receiver do not have to share a secret key. The message senders must only know the public key of the receiver while the private key must be secretly preserved by the receiver.

From that set forth above, it is clear that this coding and decoding type is characterized by operating conditions tied to the secure transmission of the data between a sender and a receiver.

In the present application, the digital signature (which as stated above is based on the use of asymmetric key encryption systems) is in substance also used in the absence of an actual transmission of information.

In fact, according to the use of the present invention, the digital signature constitutes a local method (which operates on a simultaneous peer-to-peer matching, thus in real time without any remote transmission of the data) in order to solve the problem of the controlled diffusion of the confidential information contained in portable electronic memory media. The specificity of the application is inferred from the particular function carried out by the entities involved in the process of controlling the information diffusion.

Indeed, the particular role covered by the figure of the "interlocutor" is quite clear, i.e. this is the individual who is authorized to manage the confidential digital information belonging to the other person and contained in the related "proprietor" medium (the management of the confidential digital information of the proprietor being made if and only if the recognition of the interlocutor identity has taken place). Therefore, on the basis of the use of the digital signature, the interlocutor affixes his distinctive mark on the digitalized and stored data and, by means of such digital signature, anyone can then verify the authenticity, i.e. verify i—if the data was written by the designated interlocutor, and
ii—the integrity of the signed information, i.e. will be able to control if the data was modified by someone else who is not the interlocutor.

The role of the "proprietor" should be noted in this context. He is the individual proprietor of the confidential digital information stored on the portable electronic medium (indicated above also with the term "Proprietor Medium") which is assigned by the administrator and thus owned by the same proprietor, who can view and disclose his own data, even if he cannot modify it.

From the combination and interfacing of the two roles and on the basis of the functioning of the digital signature based on asymmetric key (which is characterized in this context in that the keys have a different use with respect to their use for coding and certified data transmission), it results on one hand that the interlocutor signs the stored data, using his private key, while on the other hand the proprietor or other people who can check the authenticity or integrity of the data itself use the public key.

Indeed, beginning with the starting data, the interlocutor via his private key generates a fingerprint, i.e. a brief binary sequence of fixed length, which is coded by using his own private key; the result is the so-called digital signature, which thus constituted is queued to the stored data. The fingerprint is generated by using the so-called randomization or hash function, with the guarantee that different fingerprints are obtained starting from different data.

The interlocutor, the proprietor or the delegate who wishes to control the authenticity of the data must then use the public key in order to verify the correctness of the digital signature. Having the text non-encoded and using the hash function, the fingerprint of the document is calculated; then, using the public key, the proprietor or anyone else can verify the authenticity of the data by finding the calculated fingerprint affixed by the interlocutor/signatory. If the two fingerprints coincide, it is presumed that the document was signed by the right interlocutor and is integral, i.e. it was not modified.

After the insertion of the digital signature, each modification of the information leads to a modification of the associated fingerprint. Having the original fingerprint of the digital signature available, the interlocutor, the proprietor and the administrator of the service can quickly check if the stored digital data has been modified. With the transposition of the system with digital signature in the context of the present invention, there are essentially three cascade security levels which allow managing the access procedures with maximum reliability:

a—the separate verification of two different biometric IDs;
b—the matching between interlocutor and proprietor during the updating and writing of the data;
c—the authentication of the information set being stored by means of algorithms operating on asymmetric keys.

Moreover, the pair of public and private keys (introduced based on the use of the digital signature instrument and used for signing and verifying the stored data) are commonly granted, as is by now standardized by various certification bodies who ensure the identity of the interlocutor in possession of the private keys. This solution type optimally combines with the practical instrument currently employed for preserving the keys, constituted by the so-called smart-cards which in the embodiment according to the invention can (evidently in an effective manner) be physically integrated within containers in the portable electronic memory media.

For the purpose of authentication, which consists of establishing if an individual is really who he declares to be, one associates the use of the present finding for the identification, which consists of determining if a person can be associated (correspond) with one of the people present in the archive of the "interlocutor" medium.

The flexibility of the current operating systems is also advantageous for the obtainment of the present finding, both with regard to the permission management and with regard to the use of the user and group accounts.

Considering that we started from the assumption that the functions of acquisition, modification and cancellation of the confidential information on the proprietor medium are not allowed for the proprietor, who is only permitted to view the stored data, while the functions of acquisition, modification, cancellation and display of the stored information are all allowed for the "interlocutor" entity, an extremely useful characteristic of the operating system is one that allows organizing the users and groups, managing the resource and file access privileges based on permissions which were conferred to the user in configuring the file system. For example, commands like Useradd are effective that allow automatically assigning a unique user identifier (UID) and a unique initial group identifier (GID). In particular, with the –g option, the Useradd command allows specifying one or more supplementary groups to which the user can belong. By means of this option, a logical subdivision is implemented of the proprietor users and the interlocutor users of the system, which in this manner have select/limited access to the resources on the basis of the permissions specified for the groups they belong to.

In the specific implementation, it is clear that already in the design phase of the file system, the directive is established by the administrator (the organization managing the service which assigns the storage devices to the authorized subjects, manages the delegates etc.) to have, for the interlocutor entity (account), the active attributes on the data archives of each proprietor user belonging to his own group, and to arrange instead only one reading permission for each proprietor user, just for each related confidential stored data file. The structure that arises therefrom is the classic tree configuration, containing as many roots as there are active interlocutor entities, which are associated with groups of users only permitted accessibility to read their own data (file).

Well-known is the management according to which each user, when connected with the operating system, is connected with his primary group. This is the group that specifies the appropriate default group and is prearranged during the configuration of the file system by the administrator. When the user is connected with his primary group, he can access the files and he can only execute the programs that are associated with his group. If a user wishes to access files or programs which are not in his primary group, he can switch to a group associated with the particular file or program. The user must however be a member of such group in order to be able to switch into the other operating condition. This is clearly an optimal means for controlling the security of the data and the programs which work on this data. As an example of this activation type, it is sufficient to note the Newgroup command, which is associated with a syntax of the command, such as CAT Exam Display Newgroup etc.

Figure 2:
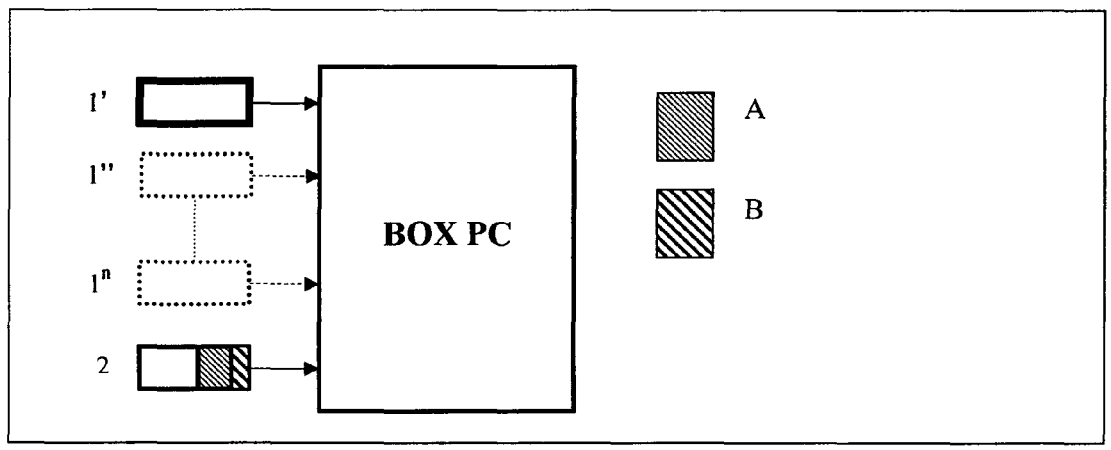
FIG. 2 is a block diagram which enters into the specifics of the permissions attributed to the user, to the group to which he belongs and to the related interlocutor.

Therefore, the interlocutor will be able to exclusively modify the subset of data present in the pertaining "proprietor" medium, i.e. manageable by the group to which he belongs, and he will not be able to access the data pertaining to other groups. FIG. 2 demonstrates that explained above, indicating with the thin hatch lines A the area controlled by the interlocutor medium 1 and with the thick hatch lines B the area controlled by the nth interlocutor medium.

Figure 3:
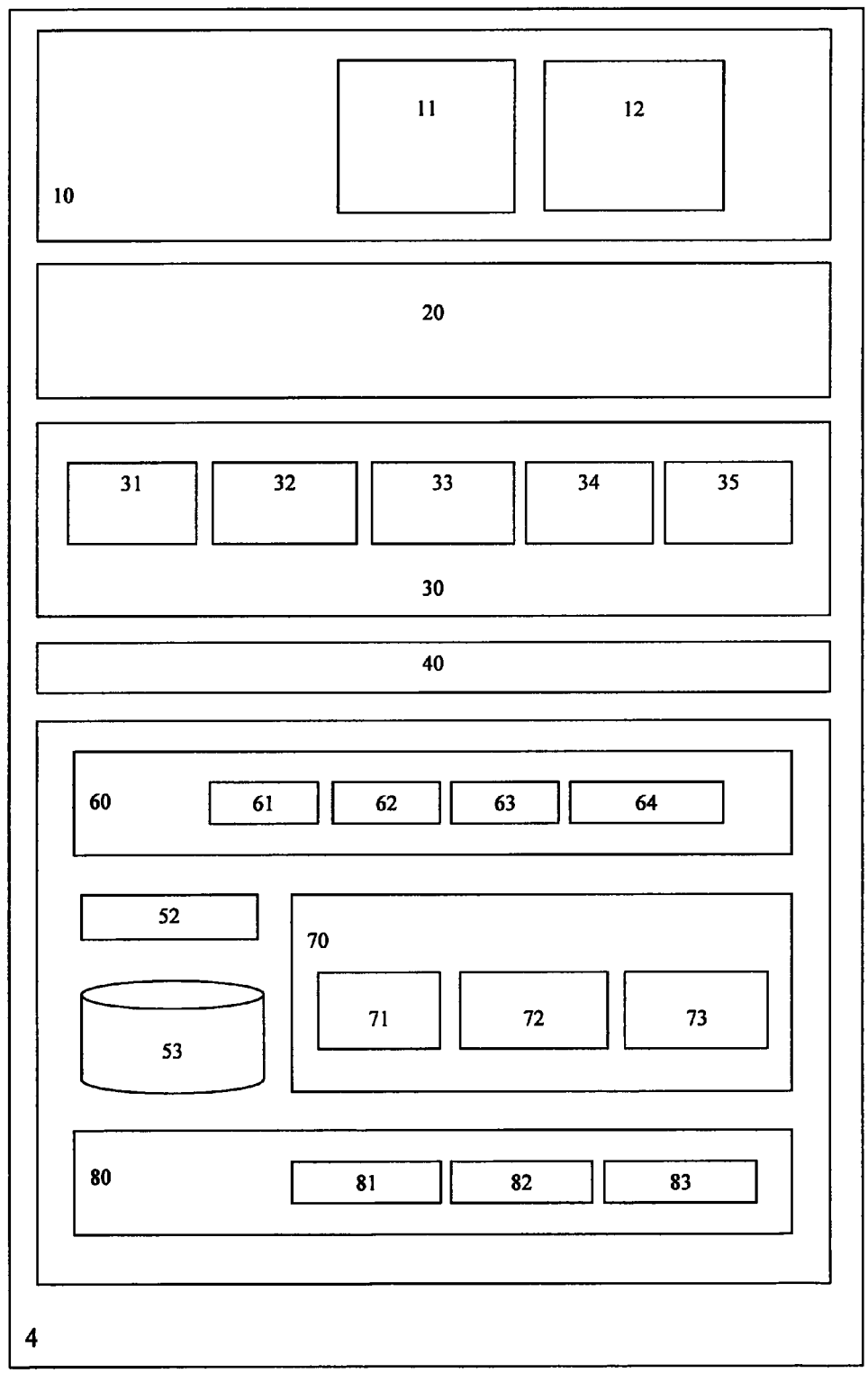
FIG. 3 is a schematic representation of the architecture of the authentication and identification system according to the present invention.

The implementation details of the present invention are represented below, considering FIG. 3 in which the following reference blocks are reported:

4 Base authentication and identification unit
10 Application Level
11 User Applications
12 Biometric Recognizer
20 Server of the essential applications (Middleware: programs which allow interworking between the different applications and components SW)
30 Interfaces
31 CAPI Cryptographic API
32 PKCS#11 standard for Public Key Cryptography
33 WS-Trust security management protocol
34 Legacy Regulations for managing the data in the relative transfer
35 API Application programming interface residing in the File System
40 Mass memory
60 Security Token Formats—packet formats dedicated to security
61 X509 Standard ITU-T for public key infrastructures
62 OTP One time password—Generation system of single disposable keys
63 SAML Security Assertion Markup Language Derivative XLKM designed for the exchange of authentications
64 User identification
52 User
53 Mass memory with reserved access
70 Digital Identity
71 Info Card media set for storing the personal data information and the rights of the PROPRIETOR user
72 Certificates
73 Private keys
80 User authentication
81 Authentication with Biometric identification
82 Authentication by means of Password
83 Authentication with Biometric identification and Password It is necessary to distinguish between the three different possible scenarios:

Scenario 1: SUPPORT, wherein the devices are managed by the ADMINISTRATOR, in which the user information is inserted, modified and cancelled.

Scenario 2: MODIFICATION, wherein the information stored in the PROPRIETOR device is modified by the INTERLOCUTOR device in a dependent, synchronous manner, so that both interact by means of a physical or even virtual PC BOX.

Scenario 3: READING, wherein the information stored in the INTERLOCUTOR device and in the PROPRIETOR device is displayed by the respective PROPRIETOR and INTERLOCUTOR users in an independent manner from each other, since each device is connected to different PC BOXES with no interaction between them.

Scenario 1: Support

1. The ADMINISTRATOR prearranges, in the hardware devices capable of managing via API 35, the encryption token components, the biometric recognition components and the mass memory components with which it is provided, and configures them with the following software applications:
    User Application with the functionalities requested on the basis of the context in which the system (medical, military, company, etc.) will operate, indicated with the user application term 11.

Biometric Configuration Application related to the dedicated application

Main Management Application defined based on BAS 20.

Application which allows the insertion of his digital certificate, which will allow the access to the administration functions by means of private key insertion.

2. The ADMINISTRATOR enables the INTERLOCUTOR device and the PROPRIETOR device upon the acquisition of their biometric properties through the insertion of the devices in a PC BOX, using the biometric configuration application related to the dedicated application. The templates of the acquired biometric properties are stored inside the devices and can only be modified by the ADMINISTRATOR himself who has the writing access rights.

3. The biometric properties are also acquired of the DELEGATE who will substitute the PROPRIETOR user in only the data reading and writing operations, and his own digital certificate will be used.

4. Stores the digital certificate of the INTERLOCUTOR user granted by the CA (Certification Authority) in the token of the INTERLOCUTOR device.

5. Stores the digital certificate of the PROPRIETOR user granted by the CA (Certification Authority) in the token of the PROPRIETOR device.

6. Stores the digital certificate of the DELEGATE user granted by the CA (Certification Authority) in the token of the PROPRIETOR device.

7. The digital certificate granted by the CA can be stored in the token of the PROPRIETOR device, so that it can be used in contexts where the PROPRIETOR will also be required to digitally sign the documents.

Scenario 2: Modification i. The INTERLOCUTOR device is inserted in a PC BOX and the Operating System of the PC BOX enables the external medium and processes the executable file, related to the dedicated application, which is stored in the file system zone of the related INTERLOCUTOR device.

ii. The enrollment process is started for the recognition of the user who is asked to present his biometric characteristics and, if requested, also the password to ensure a "strong" type authentication to the INTERLOCUTOR device which detects and compares with those stored in the mass memory (FIG. 3).

iii. In the case of positive outcome, the BAS 20 is processed, which by means of a communication protocol verifies the presence of the PROPRIETOR device. If the device is not present, the user is asked to decide whether he will proceed, and in such case scenario 3 begins, otherwise the insertion of the PROPRIETOR device is requested.

iv. The PROPRIETOR device is inserted in the PC BOX and the Operating System of the PC BOX enables the external medium and processes the executable file, related to the dedicated application, which is stored in the file system zone of the related PROPRIETOR device.

v. The enrollment process is started for the recognition of the user who is asked to present his own biometric characteristics to the PROPRIETOR device, which detects and compares them with those stored in the mass memory (FIG. 3). In this case, the typing of a password cannot be requested since the PROPRIETOR will never have to "sign" anything, so that an authentication of "strong" type is not indispensable; moreover such "strong" authentication would prevent data viewing (see Scenario 3) in case of unconsciousness of the PROPRIETOR user, who could not present the password beyond the biometric properties.

vi. In the case of positive outcome, the BAS 20 is processed, which by means of a communication protocol verifies the presence of the INTERLOCUTOR device and upon receiving the search message sent by the BAS 20 of the INTERLOCUTOR device, it responds with an ACK message.

vii. An authorization request is forwarded from the BAS 20 of the PROPRIETOR device to the BAS 20 of the INTERLOCUTOR device: the step of identification of the INTERLOCUTOR begins.

viii. The BAS 20 of the INTERLOCUTOR device transmits the Info Cards 71 which contain the personal data and the rights of the PROPRIETOR user to the BAS 20 of the PROPRIETOR device.

ix. The BAS 20 of the PROPRIETOR device prearranges the mass memory portions and the relative secure mass memory portions, following the indications present in the "User" data (see FIG. 3) for the modification of the pertinent information.

x. The user application of the PROPRIETOR device is processed and other related functionalities are started.

xi. The user application of the PROPRIETOR device can request the storage of digital files coming from storages that are different from that of the PROPRIETOR device mass memory partition, enabled as a function of the INTERLOCUTOR user rights, as is better specified in the previous point ix.

xii. In addition, this digital file will have to be digitally signed by using the digital signature of the INTERLOCUTOR user, in a manner such that the authenticity and the integrity of the document can be verified. The digital signature also ensures the non-repudiation: the signer of a document transmitted cannot deny having created it. In other words, this means that the information cannot be disclaimed, as in the case of a conventional signature on a paper document in the presence of witnesses.

xiii. The BAS 20 of the INTERLOCUTOR device requests the BAS 20 of the PROPRIETOR device for the digital certificate, thus acquiring the public key of the PROPRIETOR user xiv. The BAS 20 of the INTERLOCUTOR device signs the document with the private key stored in the INTERLOCUTOR device referred to the INTERLOCUTOR user.

xv. The BAS 20 of the INTERLOCUTOR device, before forwarding the file to the BAS 20 of the PROPRIETOR device, encodes it with the public key of the PROPRIETOR user.

xvi. The BAS 20 of the PROPRIETOR device will be able to present the contents of the file when the user application 11 of the PROPRIETOR device requests it, and it can verify the authenticity of a document: in order to do so, it decodes the signature of the document with the public key of the sender, obtaining the digital fingerprint of the document, and then compares the latter with that which is obtained by applying the hash function to the received document; if the two fingerprints are equal, the authenticity and integrity of the document are ensured.

xvii. The BAS 20 of the PROPRIETOR device will never store the private key of the INTERLOCUTOR user device, so that the security of the transaction will be ensured, since there is no connection to the network and everything is carried out locally.

xviii. The BAS 20 of the INTERLOCUTOR device will store, in its own mass memory, the data related to the performed operations which will constitute a transaction log, thus a true logbook that is consultable off-line even in the absence of the PROPRIETOR device, as is better described in scenario 3. In case of record modification requests by the user application 11 of the PROPRIETOR device, the records will be stored in the database managed directly by the user application 11, the user's rights determined in the preceding point 7.

xix. In the case of request of termination of the user application 11, the BAS 20 of the PROPRIETOR device transmits the communication closure request to the BAS 20 of the INTERLOCUTOR device and both will "kill" the active processes so as to close the transactions underway and not leave any trace in the used PC BOX.

xx. Both devices are disconnected from the PC BOX.

Scenario 3: Reading

INTRODUCTION: the two users, PROPRIETOR and INTERLOCUTOR, can view the data contained in the devices in an independent manner, which does not require the presence of both devices in the same instant. Therefore, the case relative to the display of the information contained in the INTERLOCUTOR device will be described first, followed by the case relative to the display of the information contained in the PROPRIETOR device.

a. The INTERLOCUTOR device is inserted in the PC BOX and the Operating System of the PC BOX enables the external medium and processes the executable file, related to the dedicated application, which is stored in the file system zone of the related INTERLOCUTOR device.

b. The enrollment process is started for the recognition of the user who is asked to present his own biometric characteristics and, if requested, also the password to ensure an authentication of "strong" type to the INTERLOCUTOR device which detects and compares them with those stored in the mass memory (FIG. 3).

c. The user application of the INTERLOCUTOR device is processed and the relative functionalities are started.

d. The information display functions can be requested and the BAS 20 of the INTERLOCUTOR device will retrieve, from its own mass memory, the information related to the operations carried out on the various PROPRIETOR devices.

e. Modification or supplementation functions can also be requested with regard to the information present.

f. Coding or signing activities are not requested, since if possible digital files inserted in the INTERLOCUTOR device must be transmitted, the coding will occur at the time of request, as described in point 11.

Case of Use of the Proprietor User

1. The PROPRIETOR device is inserted in the PC BOX and the Operating System of the PC BOX enables the external support and processes the executable file relative to the dedicated application, which is stored in the file system zone of the related PROPRIETOR device.
2. The enrollment process is started for the recognition of the user who is asked to present his own biometric characteristics and, if requested, also the password to ensure a "strong" type authentication to the PROPRIETOR device which detects them and compares them with those stored in the mass memory (FIG. 3).
3. The user application 11 of the PROPRIETOR device is processed and the relative functionalities are started.
4. The information display functions can be requested and the BAS 20 of the PROPRIETOR device will retrieve, from its own mass memory, the information related to the operations carried out on the various PROPRIETOR devices.
5. Modification or supplementation functions cannot be requested with regard to the information presence, since the PROPRIETOR will only be able to view the data and/or files, he will not be able to modify them.
6. Coding or signing activities are not requested.

The components of the system known as Bee Pen System use the method that is the object of the present invention. The components, both hardware and software, were designed for managing the entire user-administrator process of the service, also prearranging the technological instruments which prevent the loss of information in case of loss and/or theft of the device, whether PROPRIETOR or INTERLOCUTOR.

Current Testing

A real application of the method will now be described that has already been obtained for testing in the health field, and in particular organ transplants.

Summary

Study for the use of the health use storage device as a method for managing the health data in the follow-up step of patients who have undergone an organ transplant.

Introduction:

The follow-up step undertaken by the Transplant Centers which carried out the surgery is achieved via programmed visits, subjecting the patient to frequent studies. The massive production of paper produced by the studies is an organizational and media difficulty, since it obliges the patient to allow health workers to view all of it (such workers request this in order to have the necessary services). These services can also be requested beyond the area of competence of the Health Services Agency which normally treats the transplanted patient: if, for example, the patient is situated in a tourist location or is on a business trip, it is necessary to remember to bring the "ring binder" containing the entire clinical history each time. In this context, added value would be provided by technological systems that allow containing the entire clinical history of the patient (including study reports) in a portable medium, which protects the access with respect to non-authorized people.

Objectives:

The objective of the study is to evaluate the testing protocol acceptability of the system for controlled diffusion of the information by using a pair of memory devices with biometric recognition by the patient and the opinion of the health workers on the system itself in terms of practicality of use and utility in clinical information management.

Study Design:

Multicenter perspective study

Population involved in the testing:

60 enrolled patients looked after at the transplant center structures which participate in the testing 20 enrolled doctors from among the personnel of the transplant centers which participate in the testing Methods:

The enrolled patients will be given a pen drive, a device equipped with memory and fingerprint recognition which is inserted in a USB port present in all computers on the market. The code of this health-use storage device, associated with the personal data of the patient, will be registered in a global registry and initialized at the time of delivery, storing the fingerprints of the patient himself on the same health-use storage device. This is accomplished through a secure and protected access method that will ensure privacy. The enrolled patients will be looked after for six months after the delivery, and the data will be updated with every enrolled doctor visit.

The enrolled doctors will also be given a pen drive, and the same method will be actuated for the initialization.

At the end of the study, the patient and the testing doctor will compile a form on the acceptability and the adverse events, and they will provide an overall opinion with regard to its utility.

Main Outcome Measures:

Measures of acceptability, ease of delivery and initialization as well as use of the system. Utility potential perceived by patients and doctors. Frequency of undesired effects.

Affected Services:

Day hospital, radiology, test laboratory, virology laboratory

Activation of the system with the portable storage device for health use

The health-use storage device is a technological system for controlling the management and the diffusion of confidential digital information contained in portable electronic media, with particular regard to information of interest for the users of the system itself.

In particular, in the present case, it allows the management of the health information.

The system is composed of a series of portable electronic devices and by an administration center. The portable device is similar to a pen drive commonly used for storing the digital data produced by a computer, which over time has substituted the functions of the magnetic disk. It is connected to a standard USB port, by now found on all computers, and is equipped with a medium for the recognition of the digital fingerprint which allows activating the display of one's data, after affixing one's finger or that of the delegate.

The system provides for the use of two pen types: one for the patient and one for the doctor.

The patients will be equipped with such device defined PATIENT PEN.

The doctors will also be provided with such device defined DOCTOR PEN.

The system consists of ensuring that the data present in the PATIENT PEN can only be modified if a DOCTOR PEN is present in the computer, such pen having been activated by the affixing of the doctor's fingerprint. Each DOCTOR PEN will be able to modify all of the PATIENT PENS.

The patient can connect the PATIENT PEN to any one computer, after having carried out the recognition procedure of his own fingerprint or that of a delegate thereof, and he will be able to view the data which will be automatically brought forth; he will be able to display the data to all the people he believes should see it. This operation will be possible, for example, in the case of health emergency, by simply carrying out the recognition procedure—even via the nurse/aid workers, using the finger of the patient. The DOCTOR PEN will instead only keep track of the operations carried out on the various PATIENT PENS examined and will not keep track of the health data, which will always remain in the PATIENT PEN. The information will be viewed by the doctor at any time by inserting his DOCTOR PEN in any one computer after having carried out the recognition procedure of his fingerprint, so as to ensure the confidentiality and the non-alterability of the data.

The management system, directed by the sponsor, will have the task of operating on the electronic medium which will have the data, mainly for carrying out the following operations:

Packaging of the device;
Management of the delegates;
Collection of information from the device, of statistical and economical type;
Technical/organizational support at the transplant centers;

The test study organization will comprise the following steps:

Census of the enrolled patients and doctors in a central database

Electronics situated at the technological systems of the Lazio Regional Agency for transplants and connected pathologies Distribution of the pens and relative acquisition of the fingerprints of the patients and/or their delegates Insertion, in every PATIENT PEN, of the personal data and all other information provided for the pen-patient association Insertion, in every DOCTOR PEN, of the personal data and all other information provided for the pen-doctor association Training of the enrolled doctors Execution of the visits and relative updating of the clinical data information on the PATIENT PEN Monitoring Final report Evaluation Methods The procedure evaluation will be carried out both by the patient and the tester-doctor according to the scheme provided for by the "patient form" and by the "tester form".

Technical Description of the Prototype Employed in the Study

USB pen devices were employed, provided with biometric recognition. AData pens were selected because they came within the provided budget with regard to cost-services-characteristics (after a market selection was conducted from among a number of analogous devices). Such devices are unable to manage the digital certificates because they do not have an encryption token, hence it is not possible to use the digital signature during the testing. The system based on the health-use storage device will only intervene for the controlled management of the information that can only be carried out in the synchronous presence of the two USB pens installed on the same PC.

The system will function on the most common operating systems, such as Windows Xp, Vista, Linux and MAC.

Open source products were used for the achievement of the prototype, in particular:

TrueCrypt
PAMPA (Apache, MySQL, Php)
Autoit

The software programs were exclusively distributed on the USB pens.

A simultaneous functioning test of two pens on the same PC gave a positive result.

Two categories of pens were identified: Patient and Doctor.

The PATIENT PEN is thus configured:

TrueCrypt.exe
PatientPen.exe
VOL (volume encrypted by means of TrueCrypt)

PatientPen.exe is a compiled executable file written in AUTOIT language; it manages all the functions in order to meet the user requests. It operates directly on the PROPRIETOR device.

VOL, a file encrypted with TrueCrypt accessible by means of TrueCrypt interface activated via password, contains:

the PAMPA setting
the web pages written in php language, such pages managing the user interface by means of Internet browser
parameters.ini: configuration files which contain the identification of the PROPRIETOR device defined by the manufacturer and read via operating system API, which allows actuating a protection of the healthpen.exe software copy The DOCTOR PEN is thus configured:

DoctorPen.exe
Parameterspen.ini
LOGoperator.txt

DoctorPen.exe is a compiled executable file written in AUTOIT language; it manages all the functions in order to meet the user requests. It operates directly on the INTERLOCUTOR device.

Parameterpen.ini: configuration file which contains the first and last name of the doctor LOGoperator.txt instead contains the information regarding all the operations carried out (insertion, modification, cancellation) on the various pens of the patients (date/time/name of the patient, type of modification, new value etc.)

The PC which hosts the pens must have the single operating system installed.

No Internet connection is required.

Functioning

The insertion of the patient pen involves sending the file already pre-configured by the manufacturer for the enrollment. In case of positive outcome, the file truecrypt.exe is processed along with the file patientpen.exe, which verifies if the ID of the PROPRIETOR is equivalent to that stored in the file.ini; if the outcome is positive it presents a selection mask to the user—insert the doctor's pen or read one's own data.

In the case of selection of the second solution, the encrypted volume is opened, through an automatic insertion of the password from the patientpen.exe program on a hidden window, and the database does not allow modifications on the existing records.

On the other hand, if is requested to insert the doctor pen on the same PC, in the other available USB port, the patientpen.exe program opens a socket communication channel and is set in listening mode.

The doctor pen is inserted and after the enrollment step the doctorpen.exe file is processed by the operating system; such file writes a presence ACK on the socket channel.

At this point, patientpen.exe enables the database of the application with regard to the writing and executes the PAMPA environment which presents the user with the mask of the data stored in the PROPRIETOR device. The enabling of the database occurs because the password has passed over invisible window to the user of the encrypted volume and hence, having been previously created such that the DB update is enabled at its opening, the system results quite secure.

At the end of the operations, before the pens are taken out from the USB ports, the active process kill requests are carried out, and nothing remains installed on the host PC.

ADVANTAGES AND INDUSTRIAL USES OF THE FINDING

There are innumerable advantageous aspects of the finding and fields which would benefit therefrom. To illustrate them, we will limit ourselves to the applications in the health field, exemplified above. The service of management and controlled diffusion of confidential information contained in portable memory media can also be extended to other subjects, and also comprise the administrative workers who will have their own memory device with biometric recognition; such device will allow interacting with that of the patient and managing his administrative data, like the ticket expense amount, possible exemptions, biological testament, delegates, etc.

The service can also comprise Pharmacies, which will be provided with a memory device with biometric recognition similar to that of the doctor which will allow interacting with that of the patient, so that they can distribute the drugs only if they are digitally prescribed in the memory device with biometric recognition.

Primary care physicians will have their own memory device with biometric recognition, which will allow interacting with that of the patient in order to prescribe medicine if and only if it has not been recently prescribed; in addition they will be able to view the reports and the entire clinical history available in different languages, useful for those traveling abroad.

All of the operations carried out by the mentioned subjects are registered in the respective pens (doctors, pharmacies, primary care physicians, administrators) in a manner such that it is possible to monitor the course of the services.

The prescriptions of the primary care physicians no longer require being stamped and signed, since with the detection of his fingerprint the doctor certifies his identity and this allows digitally signing the prescription by means of electronic signature.

The use of this system permits lowering health costs by a minimum of 200 Euros/year per capita, since it simplifies the management of the relationship between the individual person and the health system with the storage of any data type on the removable medium

The invention claimed is:

1. A method for controlling a management of confidential digital information contained in portable electronic first and second medium (1, 2), comprising the steps of:

executing a first enrollment process for recognition of a first user by i) inserting the first medium (1) into a first control unit of a computing device, the first medium containing confidential digital information concerning the first user, a first biometric property concerning the first user, and a first biometric recognizer, and then ii) performing a first biometric authentication of the first user using the first biometric recognizer installed in the first medium (1) belonging to the first user to recognize the first user, wherein a first comparison between the first biometric property concerning the first user and the first biometric recognizer is performed on the first medium, wherein the first medium contains stored, in encrypted form, confidential digital information concerning a second user, wherein the first medium has stored a private key that signs updated and modified confidential digital information concerning the second user and does not store a public key associated with the encrypted confidential digital information concerning a second user stored on the second medium;

executing a second enrollment process for recognition of the second user by i) inserting the second medium (2) into the first control unit of the computing device, the second medium containing confidential digital information concerning the second user, a second biometric property concerning the second user, and a second biometric recognizer, and then ii) performing a second biometric authentication of the second user using the second biometric recognizer installed in the second medium (2) to recognize the second user, wherein a second comparison between the second biometric property concerning the second user and the second biometric recognizer is performed on the second medium, wherein the second medium contains the stored confidential digital information concerning the second user, the stored confidential digital information being in the encrypted form, wherein the second medium has stored the public key associated with the encrypted confidential digital information and that decrypts the stored confidential digital information concerning the second user and does not contain the private key;

after the first enrollment process recognizing the first user, a confirmation application stored on the first medium confirming the enrollment of the second user;

after confirming the enrollment of the second user, the first user performing management of the stored confidential digital information stored in the first and second medium with using applications prearranged in the first and second medium, and with the first and second medium being concurrently inserted in the first control unit, said management comprising the sub-steps i) transferring, from the second medium to the first medium, the confidential digital information together with the public key stored in the second medium, ii) decrypting the confidential digital information transferred from the second medium by using the public key transferred from the second medium, iii) performing at least one of a modification and an update of the decrypted confidential digital information in the first medium, iv) signing the modified or updated confidential digital information with a digital signature using the private key, and v) using the public key transferred from the second medium, encrypting the signed modified or updated confidential digital information including the digital signature, vi) forwarding the public-key encrypted confidential digital information to the second medium, and vii) storing the public-key encrypted confidential digital information in the second medium, wherein the second user can use the public key to decrypt the stored public-key encrypted confidential digital information without being able to modify the public-key encrypted confidential digital information in the second medium.

2. The method according to claim 1, wherein each of the first and second medium includes encryption token components, mass memory components, and the applications prearranged in the first and second medium have at least, i) a user application, ii) a biometric configuration application, iii) an application which allows an insertion of digital certificate allowing an access to an administrator by the private key, and iv) a main management application, which provides an interactive execution of a) CAPI cryptographic API (31), b) standard for Public Key Cryptography (32), c) security management protocol (33), and d) legacy regulations (34) for managing a data transfer.

3. The method according to claim 2, wherein the management of the confidential digital information contained in each of the first and second medium (1, 2) includes i) the second user accessing and reading the confidential digital information, which limits an accessibility for the modification of the confidential digital information stored in the second medium, ii) the first user having the accessibility for reading and writing of the confidential digital information stored in the first medium (1) and the second medium (2), and iii) the administrator assigning each of the first and second medium (1, 2) to an authorized user and limiting accessibility to the confidential digital information for reading and writing, wherein an unauthorized third party is limited to access to the confidential digital information for reading and writing stored in each of the first and second medium (1, 2).

4. The method according to claim 3, wherein a delegation operation is performed by the second user when a delegated party possess a digital medium containing the confidential digital information.

5. The method according to claim 2, wherein the first user affixes a digital fingerprint to the first medium for modifying and updating the confidential digital information by asymmetric key encryption systems, the fingerprint verifying the authentication for writing the confidential digital information and signing the digital signature in the first medium.

6. The method according to claim 2, wherein the administrator i) prearranges hardware devices for managing encryption token components, biometric recognition components, mass memory components, and software applications including at least a) user application, b) biometric configuration, c) main management application, and d) insertion of the digital certificate which allows access to the administrator via the private key, ii) enables each of the first and second medium (1, 2) to acquire biometric properties being stored inside of each of the first and second medium (1, 2) in a non-modifiable format except the administrator, iii) acquires the biometric properties of a delegate which substitutes the first user for reading and writing by using the digital certificate, iv) stores the digital certificate of the second user granted by a certification authority (CA) in the second medium (2), and v) stores the digital certificate granted by the CA in the first medium (1) for signing the digital signature.

7. The method according to claim 1, wherein the first user affixes a digital fingerprint to the first medium for modifying and updating the confidential digital information by asymmetric key encryption systems, the fingerprint verifying the authentication for writing the confidential digital information and signing the digital signature in the first medium.

8. The method according to claim 1, wherein, the management of the confidential digital information contained in each of the first and second medium (1, 2) includes an administrator controlling the confidential digital information for adding, modifying, and cancelling, the information stored in the first medium (1) is modified in a dependent and synchronous manner to interact with the first control unit physically and virtually, and the information stored in the second medium (2) and the first medium (1) is displayed in an independent manner from each other.

9. The method according to claim 8, wherein the administrator i) prearranges hardware devices for managing encryption token components, mass memory components, and the applications prearranged in the first and second medium include at least a) user application, b) biometric configuration, c) main management application, and d) insertion of the digital certificate which allows access to the administrator via the private key, ii) enables each of the first and second medium (1, 2) to acquire the biometric properties concerning the first and second users being stored inside of each of the first and second medium (1, 2) in a non-modifiable format except the administrator, iii) acquires the biometric properties of a delegate which substitutes the first user for reading and writing by using the digital certificate, iv) stores the digital certificate of the second user granted by a certification authority (CA) in the second medium (2), and v) stores the digital certificate granted by the CA in the first medium (1) for signing the digital signature.

10. The method according to claim 1, wherein a display of the confidential digital information contained in the second medium (2) is performed by the steps of:

inserting the second medium (2) in the second control unit, wherein the second control unit recognizes the second medium (2) and processes the second executable file stored in the second medium (2), performing the second enrollment process to detect and compare the second biometric information, performing a user application of the second medium (2), and requesting information display functions by the second medium (2) which retrieves an operating information carried out on a multiple second medium.

11. The method according to claim 1, wherein the management used in a medical field includes a) a patient for viewing a health data stored in a patient's portable electronic medium, which the patient is unable to modify or add to the data, and b) a doctor having a doctor's portable electronic medium, which the doctor is authorized to view, write and update the data belonging to the patient.

12. The method according to claim 1, wherein the management of the confidential digital information contained in each of the first and second medium (1, 2) includes an administrator controlling the confidential digital information for adding, modifying, and cancelling, wherein the information stored in the first medium (1) is modified in a dependent and synchronous manner to interact with the first control unit physically and virtually, wherein the information stored in the second medium (2) and the first medium (1) is displayed in an independent manner from each other.

13. The method according to claim 1, the computing device includes at least a computer, a server machine, and a mobile device.

14. A method for controlling a management of confidential digital information in portable electronic first and second medium (1, 2), comprising the steps of:

an administrator prearranging, in each of a first medium and a second medium, encryption token components, biometric recognition components, biometric properties, mass memory components, an administrator digital certificate which allows the administrator medium access via an administrator private key, and software applications including at least a) a user application, b) a biometric configuration application, and c) a main management application, wherein confidential digital information concerning the second user is stored on said second medium;

the administrator storing in each of the first and second medium biometric properties respectively of a first user and a second user, the stored biometric properties being modifiable only by the administrator; and the administrator storing a digital certificate in each of the first and second medium;

a first user modifying the confidential digital information stored in the second medium in a dependent, synchronous manner, so that the first and second medium interact via a first control unit of a first computing device; and a second user reading the confidential digital information stored in the second medium as displayed by a second computing device, wherein, the step of the first user modifying the confidential digital information stored in the second medium comprises the sub-steps of i) inserting the first medium in the first control unit to perform a first enrollment process by performing a first biometric authentication of the first user using a first biometric component installed in the first medium belonging to the first user, the first biometric authentication authorizing the first user to access to confidential digital information stored in the first medium, with only the first user being able to modify and update the confidential digital information stored in both of the first and second medium, wherein a comparison between a first biometric property concerning the first user and the first biometric component is performed on the first medium, wherein, upon the first biometric authentication authorizing the first user, the first medium verifies an existence of the second medium, ii) inserting the second medium in the first control unit to perform a second enrollment process by performing a second biometric authentication of the second user using a second biometric component installed in the second medium, the second biometric authentication authorizing the second user to access to the confidential digital information stored in the second medium, and the second user being able to read the confidential digital information stored on the second medium without being able to modify or update the confidential digital stored on the second medium, wherein, a comparison between a second biometric property concerning the second user and the second biometric component is performed on the second medium, iii) with the first and second medium concurrently inserted in the first control unit transferring, from the second medium to the first medium, the confidential digital information together with a public key stored in the second medium, iv) decoding the transferred confidential digital information by using the public key transferred from the second medium, v) modifying and updating the transferred confidential digital information in the first medium, vi) signing the modified and updated confidential digital information with a first-user private key stored in the first medium, and vii) encoding the modified and updated confidential digital information with the public key transferred from the second medium, and then forwarding the encoded information to the second medium, wherein said step of the second user reading the confidential digital information displayed by the second computing device comprises the second user performing the sub-steps of:

inserting the second medium in the second control unit, wherein the second control unit recognizes the insertion of the second medium, performing the second enrollment process to authorizing the second user to access to the confidential digital information stored in the second medium, performing the user application stored on the second medium to display the confidential digital information stored on the second medium, the user application using the public key to display the confidential digital information, wherein during said sub-steps, the first medium is not accessed by the second computing device, and the second user does not have the first-user private key and therefore cannot modify the confidential digital information stored on the second medium.

15. The method according to claim 14, wherein the step of displaying the confidential digital information contained in the first medium is performed by the steps of:

inserting the first medium in the first control unit, wherein the first control unit recognizes the first medium, performing the first enrollment process to authorizing the first user to access to the confidential digital information stored in the first medium, and performing the user application stored on the first medium to display the confidential digital information stored on the first medium, wherein during said sub-steps, the second medium is not accessed by the first computing device, and the first user has the first-user private key and therefore enables to modify the confidential digital information stored on the first medium.

* * * * *